US009265728B2

(12) United States Patent
Yuk (10) Patent No.: US 9,265,728 B2
(45) Date of Patent: Feb. 23, 2016

(54) BIOCOMPATIBLE PARTICLES AND METHOD FOR PREPARING SAME

(71) Applicant: Korea University Research and Business Foundation, Seoul (KR)

(72) Inventor: Soon Hong Yuk, Chungcheongnam-do (KR)

(73) Assignee: Korea University Research and Business Foundation

( * ) Notice: Subject to any disclaimer, the term of this patent is extended or adjusted under 35 U.S.C. 154(b) by 0 days.

(21) Appl. No.: 14/373,247

(22) PCT Filed: Dec. 6, 2012

(86) PCT No.: PCT/KR2012/010561
§ 371 (c)(1),
(2) Date: Jul. 18, 2014

(87) PCT Pub. No.: WO2013/108991
PCT Pub. Date: Jul. 25, 2013

(65) Prior Publication Data
US 2015/0010616 A1    Jan. 8, 2015

(30) Foreign Application Priority Data
Jan. 18, 2012    (KR) ........................ 10-2012-0005862

(51) Int. Cl.
*A61K 9/127*    (2006.01)
*A61K 47/48*    (2006.01)
*A61K 9/51*    (2006.01)
*A61K 9/16*    (2006.01)
*A61K 31/337*    (2006.01)
*A61K 38/27*    (2006.01)

(52) U.S. Cl.
CPC ............. *A61K 9/1271* (2013.01); *A61K 9/1641* (2013.01); *A61K 9/1682* (2013.01); *A61K9/5146* (2013.01); *A61K 31/337* (2013.01); *A61K 38/27* (2013.01); *A61K 47/48815* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| 6,991,805 B1* | 1/2006 | Hui et al. ..................... 424/450 |
| 2004/0087528 A1* | 5/2004 | Levy et al. ..................... 514/44 |
| 2005/0260260 A1* | 11/2005 | Kisak et al. ................... 424/450 |
| 2006/0153923 A1* | 7/2006 | Fernandez et al. ............ 424/489 |
| 2010/0310636 A1* | 12/2010 | Sharma et al. ................ 424/450 |

FOREIGN PATENT DOCUMENTS

| KR | 10-2009-0013848 A | 2/2009 |
| KR | 10-2011-0014877 | 2/2011 |
| KR | 10-2012-0046595 | 5/2012 |

OTHER PUBLICATIONS

KS Oh, H Lee, JY Kim, EJ Koo, EH Lee, JH Park, SY Kim, K Kim, IC Kwon, SH Yuk. "The multilayer nanoparticles formed by layer by layer approach for cancer-targeting therapy." Journal of Controlled Release, vol. 165, 2013, pp. 9-15, available online Oct. 24, 2012.*

* cited by examiner

*Primary Examiner* — Isaac Shomer
(74) *Attorney, Agent, or Firm* — Mintz Levin Cohn Ferris Glovsky and Popeo, P.C.; Fred C. Hernandez; Linyu L. Mitra (57) ABSTRACT

Biocompatible particles, according to the present invention, have encapsulated nanoparticles comprising a liposome including a drug therein, and comprise a PEO-PPO-PEO copolymer which is associated on a surface of the liposome. The biocompatible particles, according to the present invention, can flexibly control a drug release rate regardless of the solubility unique to the drug due to increased stability in an aqueous solution, thereby exhibiting continuous drug release. Also, the present invention exists stably in a powder form, thereby providing convenience for storage and administration. Therefore, the biocompatible particles according to the present invention can be useful as a drug delivery carrier.

10 Claims, 8 Drawing Sheets

BIOCOMPATIBLE PARTICLES AND METHOD FOR PREPARING SAME

CROSS-REFERENCE TO RELATED APPLICATIONS

This application is a national stage application, filed under 35 U.S.C. §371, of International Application No. PCT/KR2012/010561, filed Dec. 6, 2012, which claims priority to and the benefit of Korean Patent Application No. 10-2012-0005862, filed Jan. 18, 2012, the contents of which are incorporated herein by reference in their entireties.

TECHNICAL FIELD

The present invention relates to biocompatible particles and a method of preparing the same, and more particularly, to biocompatible particles stably exhibiting a continuous drug release pattern and having excellent storage stability, and a method of preparing the same.

The present invention claims priority to and the benefit of Korean Patent Application No. 10-2012-0005862, filed on Jan. 18, 2012, the disclosure of which is incorporated herein by reference in its entirety.

BACKGROUND ART

Most drugs are classified into hydrophobic and hydrophilic drugs. Hydrophobic drugs exhibit limited solubility in an aqueous solution, and thus are difficult to be effectively delivered in vivo. Hydrophilic drugs exhibit excellent initial expression of drug effects due to high solubility, but encounter difficulties in continuous drug release, and thus require frequent drug administration. To overcome these difficulties, development of various drug delivery carriers using nanoparticles has continued, and studies on polymeric drug delivery carriers, lipid drug delivery carriers, and nano tubes are actively progressing. As a polymeric drug delivery carrier, a polymer-drug conjugate, a polymer micelle, or a dendrimer is used.

However, such drug delivery carriers exhibit fast drug release due to instability in an aqueous solution, and particularly, when an hydrophilic drug or protein drug and antibodies are loaded, fast drug release is induced due to excellent solubility in an aqueous solution, thereby making it difficult to realize desired drug effects. To overcome this problem, repeated drug administration is required, and in the case of an expensive protein drug or antibody, an increase in treatment cost is expected.

Meanwhile, since a liposome may be composed of several kinds of lipid molecules, and most phospholipids constituting the liposome are not toxic or harmful to a human body, it is receiving attention as an effective drug delivery carrier. In Korean Patent Publication No. 0792557, liposome-type nanoparticles prepared and used as a drug delivery carrier are disclosed.

However, physical stability is not ensured in particles using a liposome, and therefore various studies to ensure stability have been attempted. For example, a specific surfactant was added to a liposome to induce an increase in stability, electrostatic charge lipids were added to components for a liposome, or sterols, anionic lipids or spingo lipids were introduced. To this end, studies to enhance stability of a liposome have been continuously performed, but the techniques have not exhibited sufficient physical stability, and thus utilization in the pharmaceutical field has been limited.

Therefore, development of new types of biocompatible particles which may increase safety in an aqueous solution, maintain an excellent redistribution function in the aqueous solution when prepared in a powder type, and flexibly control a drug release rate, thereby exhibiting a continuous drug release pattern, is required.

DISCLOSURE

Technical Problems

The present invention is directed to providing biocompatible particles which stably exhibit a sustained release pattern and have excellent storage stability.

The present invention is also directed to providing a pharmaceutical composition including the biocompatible particles.

The present invention is also directed to providing a method of preparing the biocompatible particles.

Technical Solutions

One aspect of the present invention provides biocompatible particles in which nanoparticles containing a drug are encapsulated in a liposome and a poly(ethylene oxide)-poly(propylene oxide)-poly(ethylene oxide) (PEO-PPO-PEO) copolymer associated on a surface of the liposome.

Another aspect of the present invention provides a pharmaceutical composition including the biocompatible particles.

Still another aspect of the present invention provides a method of preparing biocompatible particles, which includes: preparing nanoparticles by mixing a drug with at least one polymer selected from the group consisting of a PEO-PPO-PEO copolymer, poly(lactide-co-glycolide) (PLGA), poly caprolactone (PCL), poly(lactic acid) (PLA), poly(glycolic acid) (PGA), polyethylene glycol, and polysorbate; preparing a liposome in which the nanoparticles are encapsulated by mixing the nanoparticles with a liposome aqueous solution; and mixing the liposome with a PEO-PPO-PEO copolymer aqueous solution and freeze-drying the resulting mixture.

Advantageous Effects

According to biocompatible particles and a method of preparing the same of the present invention, biocompatible particles which are stable regardless of solubility of a drug, exhibit a continuous release pattern, and have excellent storage stability can be provided.

MODES OF INVENTION

The present invention provides biocompatible particles in which nanoparticles containing a drug are encapsulated in a liposome and a poly(ethylene oxide)-poly(propylene oxide)-poly(ethylene oxide) (PEO-PPO-PEO) copolymer is associated on a surface of the liposome.

A pharmaceutical composition of the present invention includes the biocompatible particles.

In addition, the present invention provides a method of preparing biocompatible particles, which includes: preparing nanoparticles by mixing a drug with at least one polymer selected from the group consisting of a PEO-PPO-PEO copolymer, PLGA, PCL, PLA, PGA, polyethylene glycol, and polysorbate; preparing a liposome in which the nanoparticles are encapsulated by mixing the nanoparticles with a liposome aqueous solution; and mixing the liposome with a PEO-PPO-PEO copolymer aqueous solution and freeze-drying the resulting mixture.

The terms used herein are not used to limit the present invention, but merely used to explain exemplary embodiments. Unless clearly defined otherwise in the context, singular expressions include plural expressions. It should not be understood that the words "comprise," "include," and "have" merely designate the presence of features, numbers, steps, elements and/or combinations thereof, and do not previously exclude the possibility of the presence or addition of at least one characteristic, number, step, element, and/or combination thereof.

The present invention includes various modifications, and various types, and thus will be described in detail with reference to specific examples. However, it should be understood that the present invention is not limited to specific disclosures, but includes all modifications, equivalents and/or alternatives included in the scope and claims of the present invention.

Hereinafter, biocompatible particles and a method of preparing the same according to the present invention will be described in detail.

Biocompatible particles according to an exemplary embodiment of the present invention include encapsulated nanoparticles containing a drug in a liposome, and a PEO-PPO-PEO copolymer associated on a surface of the liposome.

Figure 1:
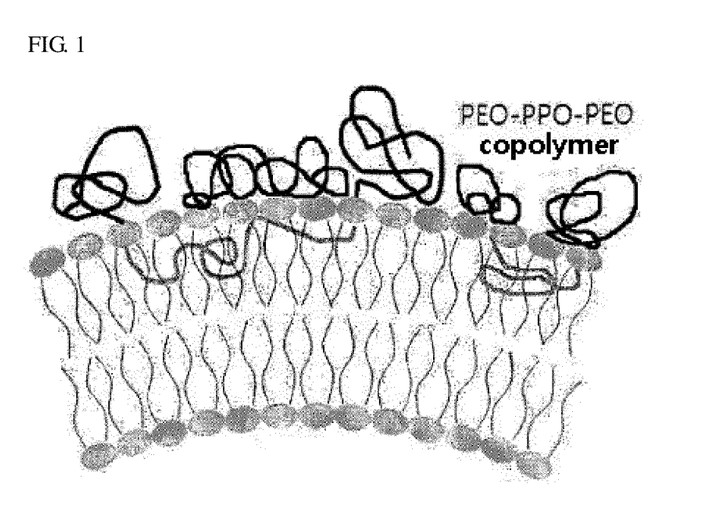
FIG. 1 is a schematic diagram of biocompatible particles according to the present invention in which a PEO-PPO-PEO copolymer is associated on a surface of a liposome.

FIG. 1 is a schematic diagram showing biocompatible particles of the present invention in which a PEO-PPO-PEO copolymer is associated on a surface of a liposome.

The term "association" used herein refers to a state in which a PEO-PPO-PEO copolymer is linked to a liposome by intermolecular interaction on a surface of the liposome, or interwined (crosslinked) to at least a part of a phospholipid bilayer of a liposome.

Referring to FIG. 1, the PEO-PPO-PEO copolymer is interwined (crosslinked) with at least a part of a phospholipid bilayer on a surface of the nanoparticle-encapsulated liposome, thereby stabilizing the surface of the liposome. The PEO-PPO-PEO copolymer is tightly interwined (crosslinked) with the bilayer of the liposome by passing through the bilayer of the liposome. In addition, a surface layer composed of the PEO-PPO-PEO copolymer is formed on an outer wall of the liposome and serves to stably preserve a structure of the liposome from various external factors that may make the liposome structure unstable.

In addition, the biocompatible particles of the present invention may exhibit excellent dispersibility, and thus may not be agglomerated. Therefore, when dispersed in a solution such as an aqueous solution for in vivo administration, the particles may be easily redispersed during dissolution.

The biocompatible particles of the present invention may be prepared in a fine powder type having a particle size of approximately 200 to 1,500 nm, and preferably approximately 300 to 1,000 nm. In addition, a drug is protected by a multilayer structure of a liposome and a PEO-PPO-PEO copolymer, and thus the particles have excellent storage stability.

Therefore, the biocompatible particles of the present invention, unlike a conventional liquid liposome, may be stored for a long time in a dry state, thereby providing convenience for storage, delivery and administration.

The drug encapsulated in the liposome includes, but is not limited to, an insoluble drug, a water-soluble drug, a protein drug, or an antibody. The insoluble drug refers to a drug that is difficult to solubilize due to low solubility in water, and includes all types of insoluble drugs such as anticancer agents, and agents for cardiovascular diseases such as alteriosclerosis and hyperlipidemia, but the present invention is not limited thereto. More particularly, the insoluble drug includes, but is not limited to, paclitaxel, docetaxel, pamoxin, anasterozole, carboplatin, topotecan, belotecan, imatinib, irinotecan, floxuridine, vinorelbine, gemcitabine, leuprolide, flutamide, zoledronate, methotrexate, camptothecin, cisplatin, vincristine, hydroxyurea, streptozocin, valrubicin, lovastatin, simvastatin, fluvastatin, atorvastatin, pitavastatin, pravastatin, or rosuvastatin.

According to an exemplary embodiment of the present invention, the drug may be encapsulated in the liposome in a nanoparticle type by being used alone or in combination with a polymer. In addition, when the drug is encapsulated as nanoparticles in combination with the polymer, the nanoparticles may be encapsulated in one liposome in the form of a single core or multiple cores.

The polymer may be at least one selected from the group consisting of a PEO-PPO-PEO copolymer, PLGA, PCL, PLA, PGA, polyethylene glycol, and polysorbate.

According to another exemplary embodiment of the present invention, a pharmaceutical composition including the biocompatible particles is provided.

The biocompatible particles may be dispersed in water or another solvent to be administered in vivo, thereby obtaining a pharmaceutical composition. Here, the drug encapsulated in the liposome is in a stabilized state, and thus biocompatibility may considerably increase regardless of the solubility, which is an original characteristic of the drug. Particularly, since the biocompatible particles exhibit a continuous release pattern, they may be useful in a sustained release preparation or continuous release preparation requiring continuous release in vivo for a long time. For example, the biocompatible particles of the present invention may continuously release a drug in vivo at a stable rate for several days to several months after administration in vivo.

Various types of pharmaceutical compositions can be prepared using the biocompatible particles of the present invention. That is, the biocompatible particles of the present invention may be prepared as a preparation for oral administration such as a granule, a capsule, or a tablet, or a preparation for parenteral administration such as intravenous injection, subcutaneous injection, or muscle injection by a known conventional method, and may be used as an effective drug delivery carrier through design of various pharmaceutically known excipients and dosage forms. More preferably, the pharmaceutical composition may additionally include at least one of excipients or additives generally used in the preparation of the biocompatible particles and the pharmaceutical composition, for example, a water-soluble/insoluble polymer, a disintegrating agent, a carrier, a filler, a glydent, a thickener, a solubilizer, a coloring agent, a pH controller, a surfactant, and an emulsifier.

In addition, the biocompatible particles of the present invention are prepared in a powder type having high flowability, and thus are advantageous for long-term storage. Accordingly, a pharmaceutical preparation including the biocompatible particles of the present invention has enhanced storage stability and is less vulnerable to deterioration during long-term distribution and storage.

A method of preparing biocompatible particles according to one exemplary embodiment of the present invention includes preparing nanoparticles by mixing a drug with at least one polymer selected from the group consisting of a PEO-PPO-PEO copolymer, PLGA, PCL, PLA, PGA, polyethylene glycol, and polysorbate; preparing a liposome in which the nanoparticles are encapsulated by mixing the nanoparticles with a liposome aqueous solution; and mixing the liposome with a PEO-PPO-PEO copolymer aqueous solution and freeze-drying the resulting mixture.

Figure 2:
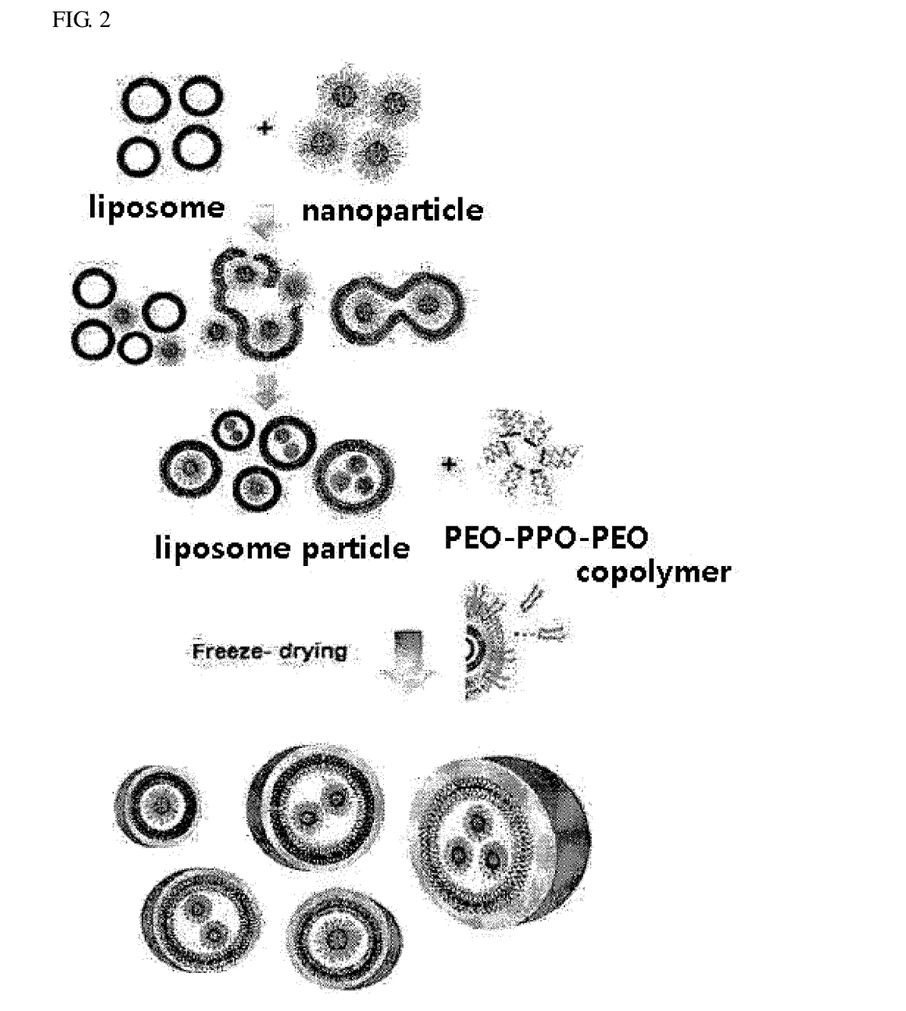
FIG. 2 is a schematic diagram showing a process of preparing biocompatible particles according to the present invention.

FIG. 2 is a schematic diagram showing a process of preparing biocompatible particles according to the present invention.

In the method of preparing biocompatible particles of the present invention, first, nanoparticles are prepared by mixing a drug with at least one polymer selected from the group consisting of a PEO-PPO-PEO copolymer, PLGA, PCL, PLA, PGA, polyethylene glycol, and polysorbate.

Specifically, the drug and the at least one polymer are mixed, and maintained at a melting point or more of each material to be prepared in a molten state. The melted product is maintained for a predetermined time, and cooled at room temperature, thereby obtaining solidified nanoparticles in an emulsion type.

The fillable drug includes, but is not particularly limited to, an insoluble drug, a water-soluble drug, a protein drug, or an antibody. The insoluble drug refers to a drug that is difficult to solubilize due to low solubility in water, and may be, but is not limited to, an anticancer agent, or an agent for a cardiovascular disease such as alteriosclerosis or hyperlipidemia, but the present invention is not limited thereto. More particularly, the insoluble drug includes, but is not limited to, paclitaxel, docetaxel, pamoxin, anasterozole, carboplatin, topotecan, belotecan, imatinib, irinotecan, floxuridine, vinorelbine, gemcitabine, leuprolide, flutamide, zoledronate, methotrexate, camptothecin, cisplatin, vincristine, hydroxyurea, streptozocin, valrubicin, lovastatin, simvastatin, fluvastatin, atorvastatin, pitavastatin, pravastatin, or rosuvastatin.

As the polymer included together with the nanoparticles, at least one selected from the group consisting of a PEO-PPO-PEO copolymer, PLGA, PCL, PLA, PGA, polyethylene glycol, and polysorbate is included.

The polyethylene glycol is a polymer represented by Formula 1.

[Formula 1]

In Formula 1, n is an integer from 3 to 1,000.

Polyethylene glycol is an amphipathic polymer having hydrophilicity and hydrophobicity. It is a liquid at a low molecular weight, and a solid at a higher molecular weight. The polyethylene glycol may be PEG 150, PEG 300, PEG 400, PEG 1000, PEG 6000, PEG 8000, PEG 10000, PEG 20000, PEG 30000, and PEG 40000 according to a molecular weight. For example, PEG 300 is polyethylene glycol having a molecular weight of 300. In addition, polyethylene glycol having a molecular weight of 10,000 refers to polyethylene oxide (PEO). Among these, PEG 400 is formed in a liquid, and is frequently used in solubilization of various types of insoluble drugs. Particularly, PEG 400 is a material for oral and parenteral use that has been approved by the US Food and Drug Administration (FDA).

According to an exemplary embodiment of the present invention, as the polyethylene glycol, PEG 400 may be used.

The PEO-PPO-PEO copolymer may be a triblock copolymer represented by Formula 2.

In Formula 2, b is an integer of 10 or more, and a+c is a number such that terminal parts ((C$_2$H$_4$O)$_a$ and (C$_2$H$_4$O)$_c$) account for 5 to 95 wt %, and preferably 20 to 90 wt % of the PEO-PPO-PEO copolymer.

Properties of the PEO-PPO-PEO copolymer depend on a ratio of a polyoxypropylene block and a polyoxyethylene block, that is, a ratio of b and a+c of Formula 2. As the PEO-PPO-PEO copolymer, a commercially available product prepared by a method disclosed in known literature or previously prepared may be used. The PEO-PPO-PEO copolymer used in the preparation method of the present invention may have, but is not particularly limited to, a molecular weight of, for example, approximately 1,000 to 16,000.

Meanwhile, the PEO-PPO-PEO copolymer is known as a poloxamer or Pluronic. Poloxamers are solid at room temperature, and dissolve in water and ethanol. According to an exemplary embodiment of the present invention, as the PEO-PPO-PEO copolymer, poloxamer 68, poloxamer 127, poloxamer 188, poloxamer 237, poloxamer 338 or poloxamer 407 may be used, but the present invention is not limited thereto. For example, the poloxamer 188 is a poloxamer having a molecular weight of approximately 8,350, which is a compound of Formula 2, in which b is 30 and a+c is 75.

As described above, nanoparticles in which a drug is fused with a polymer may be obtained by mixing a drug with at least one polymer selected from the group consisting of a PEO-PPO-PEO copolymer, PLGA, PCL, PLA, PGA, polyethylene glycol, and polysorbate.

According to an exemplary embodiment of the present invention, the preparing of the nanoparticles may be performed by mixing a drug with a polymer, and heating the mixture at approximately 60 to 90° C. for approximately 10 to 30 minutes. When the nanoparticles are prepared by heating as described above, as the polymer, a PEO-PPO-PEO copolymer, polyethylene glycol or polysorbate may be used.

According to another exemplary embodiment of the present invention, the preparing of the nanoparticles may be performed by mixing the drug with a polymer in a solvent to prepare a solution, and evaporating the solvent. Here, as the solvent, any one that can dissolve the drug may be used without limitation. In addition, as the polymer, at least one polymer selected from the group consisting of a PEO-PPO-PEO copolymer, PLGA, PCL, PLA, PGA, polyethylene glycol, and polysorbate may be used.

According to still another exemplary embodiment of the present invention, the preparing of the nanoparticles may be performed by preparing an aqueous solution by mixing the drug with the polymer and freeze-drying the resulting aqueous solution. When the nanoparticles are prepared through freeze-drying as described above, as the polymer, at least one polymer selected from the group consisting of a PEO-PPO-PEO copolymer, PLGA, PCL, PLA, PGA, polyethylene glycol, and polysorbate may be used.

In the method of preparing the nanoparticles, an evaporating or freeze-drying method after dissolution in a solvent may be useful for a drug particularly vulnerable to heat. When the nanoparticles are prepared by the evaporation or freeze-drying, thermal decomposition of the drug may be prevented, but the polymer-drug bond is weakly formed, thereby showing an unstable releasing pattern. However, according to the preparation method of the present invention, a stable releasing pattern may be shown by encapsulating the nanoparticles in a liposome, and stabilizing a surface of the liposome without strength of the polymer-drug bond.

Afterward, the nanoparticle-encapsulated liposome is prepared by mixing the nanoparticles prepared as described above with a liposome aqueous solution.

Referring to FIG. 2, the preparing of the nanoparticle-encapsulated liposome includes fusing nanoparticles and a liposome using vesicle fusion.

Here, the liposome aqueous solution used in the fusion may be obtained by ultrasonication of an aqueous solution including a phospholipid.

According to an exemplary embodiment of the present invention, a liposome aqueous solution may be prepared by preparing an aqueous solution having a content of approximately 10 to 30 wt % using lecithin as a phospholipid, and performing ultrasonication, but the present invention is not limited thereto. Liposome aqueous solutions prepared by various methods may be used. A particle size of the liposome included in the liposome aqueous solution obtained as described above is approximately 50 to 150 nm, and preferably approximately 100 nm.

Lecithin is a type of a phospholipid and is a main component of a cell membrane. It has a structure in which phosphoric acid/choline and two molecules of fatty acids are bound to glycerol.

Lecithin is a natural ingredient extracted from beans or eggs as a component of the cell membrane. Lecithin is associated with basic metabolism for life such as absorption of nutrients and secretion of waste, provides the neurotransmitter acetylcholine to help to activate the brain and treat and prevent various types of cerebropathia such as dementia, and serves as an emulsifier to dissolve cholesterol excessively present on blood vessel walls, thereby preventing cardiovascular disorders such as myocardial infarctions. In addition, lecithin stimulates adsorption of fat-soluble vitamins such as vitamin A or E, thus preventing aging. For these reasons, it is most widely used as a nutrient provided to patients after operation. Moreover, lecithin is generally administered into a body by injection (Ringer's solution), and thus has no problem in application to a human body.

The nanoparticle-encapsulated liposome prepared by the above-described method has uniform particle size distribution. According to an exemplary embodiment of the present invention, an average particle size of the nanoparticle-encapsulated liposome may be approximately 150 to 200 nm. The nanoparticles may be encapsulated in one liposome in the form of a single core or multiple cores.

The nanoparticles and the liposome aqueous solution may be prepared by mixing the nanoparticles with the liposome in a weight ratio of approximately 1:1 to 1:99, preferably approximately 1:1 to 1:20, and more preferably approximately 1:1 to 1:5.

Afterward, the nanoparticle-encapsulated liposome is mixed with a PEO-PPO-PEO copolymer aqueous solution, and the resulting mixture is freeze-dried, thereby obtaining biocompatible particles of the present invention. Here, the freeze-drying process may be performed by further adding a cryo-protective agent such as trehalose.

The detailed descriptions for the PEO-PPO-PEO copolymer have been previously provided in the step of preparing nanoparticles. According to an exemplary embodiment of the present invention, as the PEO-PPO-PEO copolymer mixed with the nanoparticle-encapsulated liposome, at least one selected from the group consisting of poloxamer 68, poloxamer 127, poloxamer 188, poloxamer 237, poloxamer 338 or poloxamer 407 may be used, but the present invention is not limited thereto. Here, the PEO-PPO-PEO copolymer is mixed in an aqueous solution state, and 5 to 30 wt % aqueous solution of PEO-PPO-PEO copolymer may be used.

According to an exemplary embodiment of the present invention, in the step of mixing the nanoparticle-encapsulated liposome with the PEO-PPO-PEO copolymer aqueous solution, a weight ratio of the nanoparticle-encapsulated liposome to the PEO-PPO-PEO copolymer may be approximately 1:0.1 to approximately 1:99, preferably approximately 1:1 to approximately 1:20, and more preferably approximately 1:1 to approximately 1:5. When too little of the PEO-PPO-PEO copolymer is included compared to the nanoparticle-encapsulated liposome, a stabilization effect of a surface of the liposome due to the PEO-PPO-PEO copolymer may be insignificant. However, when too much of the PEO-PPO-PEO copolymer is included compared to the nanoparticle-encapsulated liposome, release of the filled drug may be inhibited, and thus a desired therapeutic effect may not be realized.

The PEO-PPO-PEO copolymer is interwined (crosslinked) to at least a part of a surface of the nanoparticle-encapsulated liposome and a phospholipid bilayer to be associated, thereby serving to maintain a structure of the liposome.

The biocompatible particles of the present invention obtained by the preparation method described above may be present in fine powder, thereby having excellent dispersibility, and may be easily redispersed when dispersed and dissolved in a solution such as an aqueous solution for in vivo administration. In addition, the biocompatible particles may be prepared by a simple method using a biocompatible polymer that does not have any problem when remaining in a body and without using an organic solvent or other excipients that may have a harmful influence on a human body, thereby achieving both safety and processability. In addition, storage stability is enhanced, and thus the biocompatible particles can be widely used in preparation of a pharmaceutical composition or preparation.

Hereinafter, to help in understanding the present invention, exemplary examples will be provided. However, the examples are merely provided such that the present invention can be more easily understood, not to limit the scope of the present invention.

EXAMPLES

Example 1

Preparation of Biocompatible Particles Containing Docetaxel 0.04 g of docetaxel and 0.1 g of PEG 400 were mixed for 12 hours, thereby preparing a uniform mixture. 0.4 g of a poloxamer (polyoxyethylene-polyoxypropylene-polyoxyethylene triblock copolymer, F-68) was added to the mixture, heated at 70° C. for 10 minutes, and stirred for 5 minutes to completely melt the mixture, thereby obtaining a liquid adhesive product. After stirring, the resulting product was cooled at room temperature, thereby obtaining nanoparticles.

Separately, lecithin was prepared in an aqueous solution having a concentration of 20 wt %, and treated by ultrasonication for 10 minutes, thereby preparing a liposome aqueous solution. Here, the liposome had a particle size of 100 nm.

0.1 g of the nanoparticles solidified at room temperature were mixed with 0.8 g of the 20 wt % lecithin aqueous solution, and fusion of the nanoparticles was induced, thereby preparing a nanoparticle-encapsulated liposome. Here, the particle size of the liposome was 150 to 200 nm.

Subsequently, 0.8 g of a 20 wt % poloxamer (F-68) aqueous solution was added to 0.1 g of the nanoparticle-encapsulated liposome aqueous solution, stirred for 10 minutes, and freeze-dried, thereby preparing powder-type biocompatible particles.

Example 2

Preparation of Biocompatible Particles Containing Docetaxel 0.04 g of docetaxel and 0.1 g of PEG 400 were added to 0.4 g of a poloxamer (polyoxyethylene-polyoxypropylene-polyoxyethylene triblock copolymer, F-68) and mixed with ethanol to prepare a homogeneous mixture solution, and then the ethanol was evaporated, thereby obtaining nanoparticles.

Separately, lecithin was prepared in an aqueous solution having a concentration of 20 wt %, and treated by ultrasonication for 10 minutes, thereby preparing a liposome aqueous solution. Here, the liposome had a particle size of 100 nm.

0.1 g of the nanoparticles solidified at room temperature were mixed with 0.8 g of the 20 wt % lecithin aqueous solution, and fusion of the nanoparticles was induced, thereby preparing a nanoparticle-encapsulated liposome. Here, the particle size of the liposome was 150 to 200 nm.

Subsequently, 0.8 g of a 20 wt % poloxamer (F-68) aqueous solution was added to 0.1 g of the nanoparticle-encapsulated liposome aqueous solution, stirred for 10 minutes, and freeze-dried, thereby preparing powder-type biocompatible particles.

Example 3

Preparation of Biocompatible Particles Containing Human Growth Hormone 1 ml of a human growth hormone (100 μg/ml), 0.1 g of PEG 400, and 1 ml of a 25 wt % poloxamer (F-68) aqueous solution were mixed, thereby preparing a uniform aqueous solution. The uniform aqueous solution was freeze-dried, and thus nanoparticles in which a human growth hormone was filled were prepared.

Separately, lecithin was prepared in an aqueous solution having a concentration of 20 wt %, and treated by ultrasonication for 10 minutes, thereby preparing a liposome aqueous solution.

0.2 g of nanoparticles in which a human growth hormone was filled were mixed with 1.5 ml of a 20 wt % lecithin aqueous solution, and fusion of the nanoparticles was induced, thereby preparing a liposome in which the nanoparticles are encapsulated having a particle size of 150 to 200 nm.

Subsequently, 0.8 g of a 20 wt % poloxamer (F-68) aqueous solution was added to 0.1 g of the nanoparticle-encapsulated liposome aqueous solution, stirred for 10 minutes, and freeze-dried, thereby preparing powder-type biocompatible particles.

Example 4

Preparation of Biocompatible Particles Containing Docetaxel

Biocompatible particles were prepared by the same method as described in Example 1, except that a poloxamer (F-127) in which a polyoxyethylene block was increased in length was used instead of the poloxamer (F-68) used in Example 1.

Example 5

Preparation of Biocompatible Particles Containing Docetaxel

Biocompatible particles having a multilayer structure were prepared by the same method as described in Example 2, except that a poloxamer (F-127) in which a polyoxyethylene block was increased in length was used instead of the poloxamer (F-68) used in Example 2.

Example 6

Preparation of Biocompatible Particles Containing Human Growth Hormone

Biocompatible particles having a multilayer structure were prepared by the same method as described in Example 3, except that a poloxamer (F-127) in which a polyoxyethylene block was increased in length was used instead of the poloxamer (F-68) used in Example 3.

Comparative Example 1

Preparation of Liposome in which Nanoparticles Containing Docetaxel were Encapsulated 0.04 g of docetaxel and 0.1 g of PEG 400 were mixed for 12 hours, thereby preparing a uniform mixture. 0.4 g of a poloxamer (F-68) was added to the mixture, heated at 70° C. for 10 minutes, and stirred for 5 minutes to completely melt the mixture, thereby obtaining a liquid adhesive product. After stirring, the resulting product was cooled at room temperature, thereby obtaining nanoparticles.

Separately, lecithin was prepared in a 20 wt % aqueous solution, and treated by ultrasonication for 10 minutes, thereby obtaining a liposome aqueous solution. Here, a particle size of the liposome was 100 nm.

0.1 g of the nanoparticles solidified at room temperature were mixed with 0.8 g of the 20 wt % lecithin aqueous solution to induce fusion of the nanoparticles, thereby preparing a liposome in which the nanoparticles were encapsulated, and here, the particle size was 150 to 200 nm.

Comparative Example 2

Preparation of Liposome in which Nanoparticles Containing Docetaxel were Encapsulated 0.04 g of docetaxel and 0.1 g of PEG 400 were added to 0.4 g of a poloxamer (polyoxyethylene-polyoxypropylene-polyoxyethylene triblock copolymer, F-68), and mixed with ethanol to prepare a uniform mixture solution, and then the ethanol was evaporated, thereby obtaining nanoparticles.

Separately, lecithin was prepared in a 20 wt % aqueous solution, and treated by ultrasonication for 10 minutes, thereby obtaining a liposome aqueous solution. Here, a particle size of the liposome was 100 nm.

0.1 g of the nanoparticles solidified at room temperature were mixed with 0.8 g of the 20 wt % lecithin aqueous solution to induce fusion of the nanoparticles, thereby preparing a nanoparticle-encapsulated liposome, and here, the particle size was 150 to 200 nm.

Comparative Example 3

Preparation of Liposome in which Nanoparticles Containing Human Growth Hormone were Encapsulated 1 ml of a human growth hormone (100 μg/ml), 0.1 g of PEG 400 and 1 ml of 25 wt % of a poloxamer (polyoxyethylene-polyoxypropylene-polyethylene triblock copolymer, F-68) aqueous solution were mixed, thereby preparing a uniform aqueous solution. The uniform aqueous solution was freeze-dried, thereby preparing nanoparticles in which a human growth hormone was filled.

Separately, lecithin was prepared in a 20 wt % aqueous solution, and treated by ultrasonication for 10 minutes, thereby preparing a liposome aqueous solution.

0.2 g of the nanoparticles in which a human growth hormone was filled were mixed with 1.5 ml of the 20 wt % lecithin aqueous solution to induce fusion of the nanoparticles, thereby preparing a liposome in which the nanoparticles were encapsulated. A particle size of the liposome was 150 to 200 nm.

Comparative Example 4

Preparation of Biocompatible Particles Containing Human Growth Hormone 1 ml of a human growth hormone (100 μg/ml), 0.1 g of PEG 400 and 1 ml of 25 wt % of a poloxamer (polyoxyethylene-polyoxypropylene-polyoxyethylene triblock copolymer, F-68) aqueous solution were mixed, thereby preparing a uniform aqueous solution. The uniform aqueous solution was freeze-dried, thereby preparing nanoparticles in which a human growth hormone was filled.

Comparative Example 5

Preparation of Nanoparticles Containing Docetaxel 0.04 g of docetaxel and 0.1 g of PEG 400 were mixed for 12 hours, thereby preparing a uniform mixture. 0.4 g of a poloxamer (polyoxyethylene-polyoxypropylene-polyoxyethylene triblock copolymer, F-68) was added to the mixture, heated at 70° C. for 10 minutes, and stirred for 5 minutes to completely melt the mixture, thereby obtaining a liquid adhesive product. After stirring, the adhesive product was cooled at room temperature, thereby obtaining nanoparticles.

Experimental Example

Analysis of Particle Size Distribution

Experimental Example 1

Figure 3:
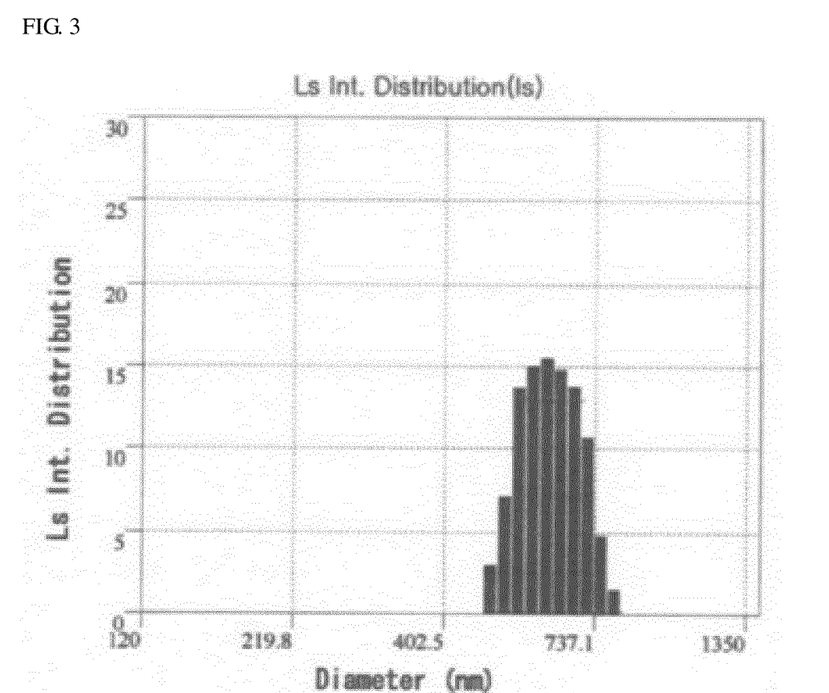
FIG. 3 shows a graph showing distribution of a particle size of biocompatible particles in Example 1 according to the present invention.

Distribution of a particle size of biocompatible particles obtained by Example 1 is shown in FIG. 3.

Referring to FIG. 3, it was seen that the biocompatible particles of the present invention showed relatively uniform particle size distribution.

Figure 4:
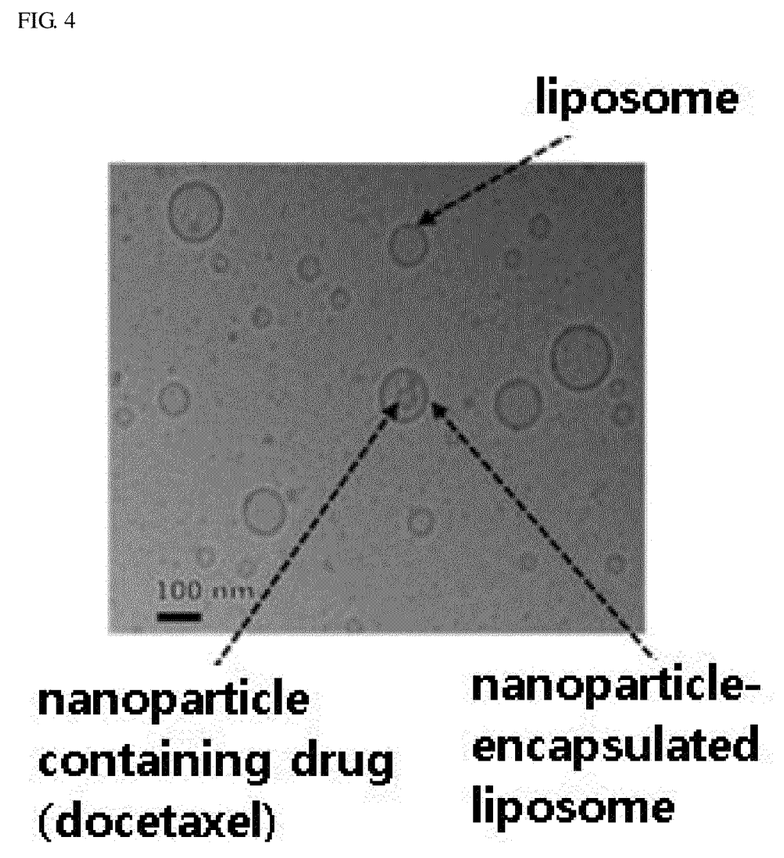
FIG. 4 is a ×30,000 magnified transmittance electron microscopy (TEM) image of a liposome including encapsulated nanoparticles containing a drug.
Figure 5:
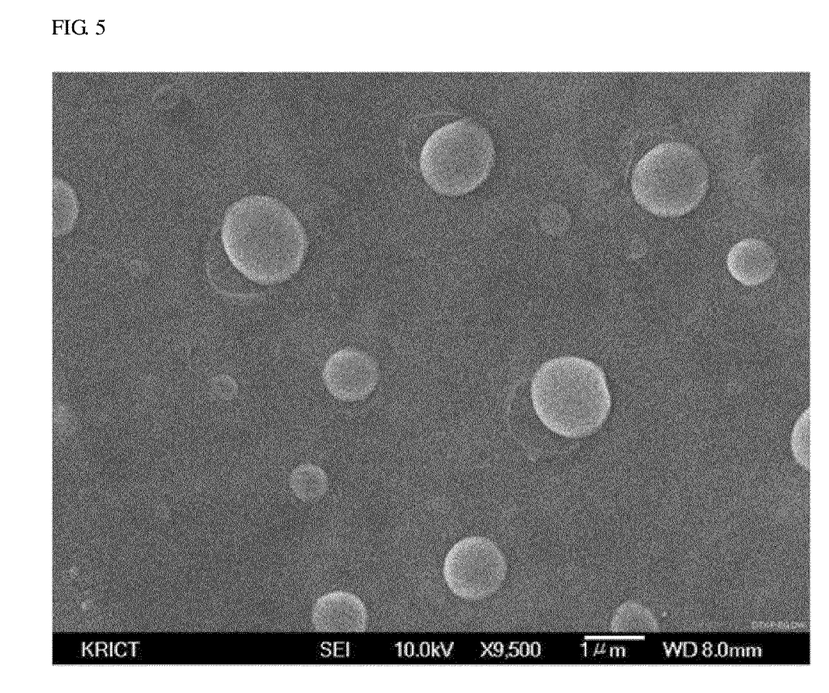
FIG. 5 is a ×9,500 magnified field emission scanning electron microscopy (FE-SEM) image of the biocompatible particles in Example 1 according to the present invention.
Figure 6:
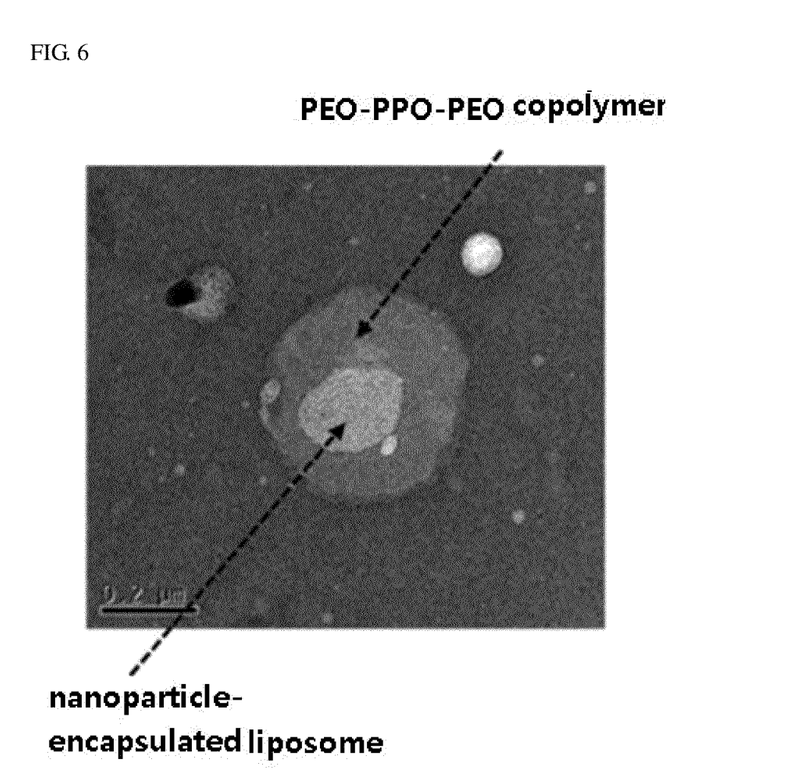
FIG. 6 is a ×30,000 magnified TEM image of the biocompatible particles in Example 1 according to the present invention.

In addition, images of the liposome and the biocompatible particles obtained by Example 1 are shown in FIGS. 4 to 6.

More particularly, FIG. 4 is a ×30,000 magnified TEM image of the liposome in which the nanoparticles containing the drug were encapsulated obtained in Example 1.

Referring to FIG. 4, it was seen that the liposome in which the nanoparticles containing the drug were encapsulated, and which had a particle size of 150 to 200 nm was produced.

FIG. 5 is a ×9,500 magnified FE-SEM image of the biocompatible particles obtained in a powder state by freeze-drying the liposome in which the nanoparticles were encapsulated in Example 1, and FIG. 6 is a ×30,000 magnified TEM image of the biocompatible particles.

Referring to FIGS. 5 and 6, it was seen that the biocompatible particles in which a PEO-PPO-PEO copolymer was associated on a surface of the liposome were produced.

Release Pattern of Drug Encapsulated in Biocompatible Particles

Experimental Example 2

To confirm a release pattern of a drug encapsulated in biocompatible particles of the present invention, the following experiment was performed.

20 mg of the biocompatible particles prepared in Example 1, the liposome prepared in Comparative Example 1, and the nanoparticles prepared in Comparative Example 5, respectively, were put into a dialysis bag (filtering limit to molecular weight—100,000), and impregnated in 20 ml of a phosphate buffer solution (PBS, pH 7.4). Here, the experiment was performed in the PBS containing 1 wt % Tween 80. The PBS was maintained at 37.5° C. and stirred at 600 rpm. After a predetermined time, 5 ml of the PBS was taken, and an amount of docetaxel released in each of Example 1 and Comparative Examples 1 and 5 was measured by HPLC. All of the remaining PBS after sampling was removed, and replaced to a fresh PBS.

Figure 7:
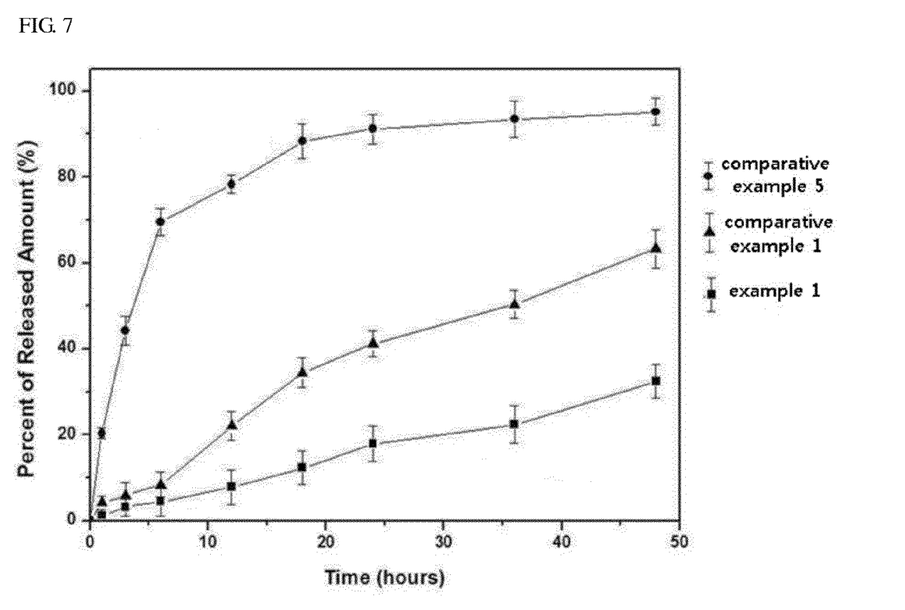
FIG. 7 is a graph showing drug release patterns of particles in Example 1 and Comparative Examples 1 and 5 according to time.

The release patterns of docetaxel in Example 1 and Comparative Examples 1 and 5 are shown in FIG. 7.

Referring to FIG. 7, it was confirmed that docetaxel had a release rate of 40% or less within 50 hours, and was slowly released at an almost same speed. Accordingly, it was seen that the biocompatible particles according to the present invention showed a stable and consistent drug release pattern.

Meanwhile, from the liposome containing nanoparticles in Comparative Example 1, release of docetaxel became approximately twice as fast as in the biocompatible particles of Example 1 over time. In addition, the nanoparticles of Comparative Example 5 showed a release rate of approximately 90% within 20 hours from the early stage, and thus would be unsuitable for application to a sustained-release preparation.

Experimental Example 3

20 mg of the biocompatible particles prepared in Example 3, the liposome prepared in Comparative Example 3, and the nanoparticles prepared in Comparative Example 4, respectively, were put into a dialysis bag (filtering limit to molecular weight—100,000), and impregnated in 20 ml of a phosphate buffer solution (PBS, pH 7.4). Here, the experiment was performed in the PBS containing 0.5 wt % Tween 80. The PBS was maintained at 37.5° C. and stirred at 600 rpm. After a predetermined time, 5 ml of the PBS was taken, and an amount of docetaxel released in each of Example 3, and Comparative Examples 3 and 4 was measured by HPLC. All of the remaining PBS after sampling was removed, and replaced to a fresh PBS.

Figure 8:
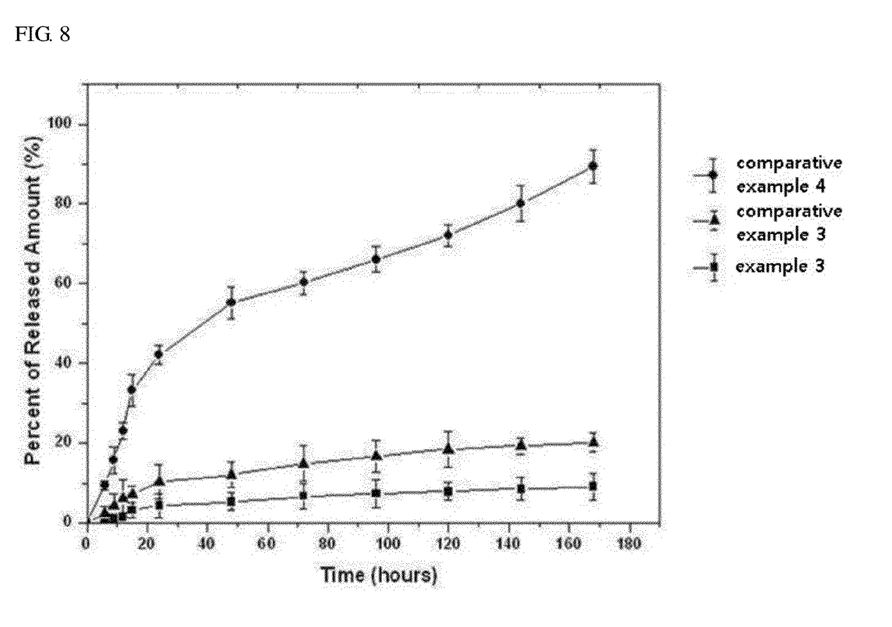
FIG. 8 is a graph showing drug release patterns of particles in Example 3 and Comparative Examples 3 and 4 according to time.

Release patterns of human growth hormones of Example 3, and Comparative Examples 3 and 4 are shown in FIG. 8.

As shown in FIG. 8, it was confirmed that a human growth hormone had a release rate of 10% or less within 160 hours, and was slowly released at an almost same speed. Accordingly, it was seen that the biocompatible particles according to the present invention showed a stable and consistent drug release pattern.

Meanwhile, from the liposome containing nanoparticles in Comparative Example 3, release of docetaxel became approximately twice as fast as in the biocompatible particles of Example 3 over time. In addition, the nanoparticles of Comparative Example 4 showed a release rate of approximately 50% within 40 hours from the early stage, and a release rate of approximately 80% within 160 hours.

Consequently, it was shown that the biocompatible particles of the present invention were suitable for a sustained drug delivery system requiring long-term continuous release since a PEO-PPO-PEO copolymer was associated on a surface of a liposome to show a stable drug release pattern.

The invention claimed is:

1. A method of preparing biocompatible particles, comprising:
    preparing nanoparticles by mixing a drug with at least one polymer selected from the group consisting of a poly(ethylene oxide)-poly(propylene oxide)-poly(ethylene oxide) (PEO-PPO-PEO) copolymer, poly(lactide-co-glycolide) (PLGA), poly caprolactone (PCL), poly(lactic acid) (PLA), poly(glycolic acid) (PGA), polyethylene glycol, and polysorbate;
    providing an aqueous solution comprising lecithin;
    mixing the nanoparticles with the aqueous solution comprising lecithin to form liposomes in which the nanoparticles are encapsulated; and
    mixing the nanoparticle-encapsulated liposome with an aqueous solution comprising a PEO-PPO-PEO copolymer and freeze-drying the resulting mixture.

2. The method of claim 1, wherein the drug includes at least one selected from the group consisting of an insoluble drug, a water-soluble drug, a protein drug, and an antibody.

3. The method of claim 1, wherein the PEO-PPO-PEO copolymer is at least one selected from the group consisting of poloxamer 68, poloxamer 127, poloxamer 188, poloxamer 237, poloxamer 338, and poloxamer 407.

4. The method of claim 1, wherein the aqueous solution comprising the PEO-PPO-PEO copolymer includes the PEO-PPO-PEO copolymer at 1 to 30 wt %.

5. The method of claim 1, wherein the aqueous solution comprising lecithin includes lecithin at 10 to 30 wt % and is prepared through ultrasonication.

6. The method of claim 1, wherein the nanoparticle and the liposome aqueous solution are mixed in a weight ratio of 1:1 to 1:99.

7. The method of claim 1, wherein the preparing of the nanoparticles is performed by mixing a drug and at least one polymer selected from the group consisting of a PEO-PPO-PEO copolymer, polyethylene glycol and polysorbate, and heating the resulting mixture at 60 to 90° C.

8. The method of claim 1, wherein the preparing of the nanoparticles is performed by mixing a drug and at least one polymer selected from the group consisting of a PEO-PPO-PEO copolymer, PLGA, PCL, PLA, PGA, polyethylene glycol, and polysorbate with a solvent to form a solution, and subsequently evaporating the solvent.

9. The method of claim 1, wherein the preparing of the nanoparticles is performed by mixing a drug and at least one polymer selected from the group consisting of a PEO-PPO-PEO copolymer, PLGA, PCL, PLA, PGA, polyethylene glycol, and polysorbate with water to form an aqueous solution, and subsequently freeze-drying the resulting solution to isolate nanoparticles.

10. The method of claim 1, wherein, in the mixing of the nanoparticle-encapsulated liposome and the aqueous solution comprising a PEO-PPO-PEO copolymer, the nanoparticle-encapsulated liposome is mixed with the PEO-PPO-PEO copolymer in a weight ratio of 1:0.1 to 1:99.

* * * * *